United States Patent [19]

Argoudelis et al.

[11] Patent Number: 4,505,895

[45] Date of Patent: Mar. 19, 1985

[54] ANTIBIOTIC $273_{a1}$

[75] Inventors: Alexander D. Argoudelis, Portage; Vincent P. Marshall, Kalamazoo; Paul F. Wiley, Portage, all of Mich.

[73] Assignee: The Upjohn Company, Kalamazoo, Mich.

[21] Appl. No.: 480,604

[22] Filed: Mar. 30, 1983

[51] Int. Cl.³ .......................... A61K 35/74; C12P 1/06
[52] U.S. Cl. ..................................... 424/117; 435/169
[58] Field of Search .......................... 424/117; 435/169

[56] References Cited

U.S. PATENT DOCUMENTS 4,335,108  6/1982  Argoudelis et al. ................ 424/117

Primary Examiner—Jerome D. Goldberg
Attorney, Agent, or Firm—Lawrence T. Welch; Roman Saliwanchik

[57] ABSTRACT

Novel and useful antibiotics designated $273a_{1\alpha}$ and $273a_{1\beta}$ can be produced in a fermentation using *Streptomyces paulus*, strain 273, NRRL 12251. These antibiotics are active against various Gram-positive bacteria. Also, these antibiotics are, advantageously, soluble in aqueous solutions.

3 Claims, 19 Drawing Figures

FIGURE 6
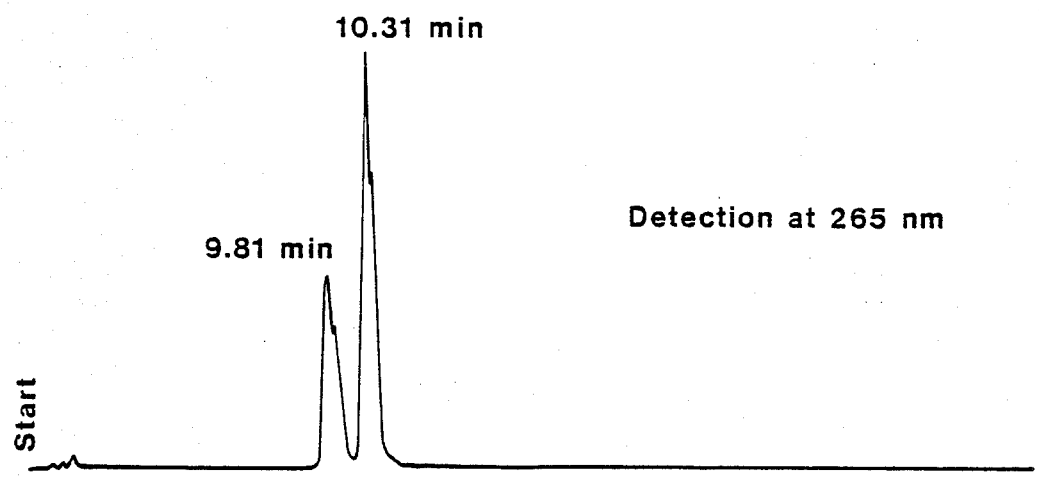
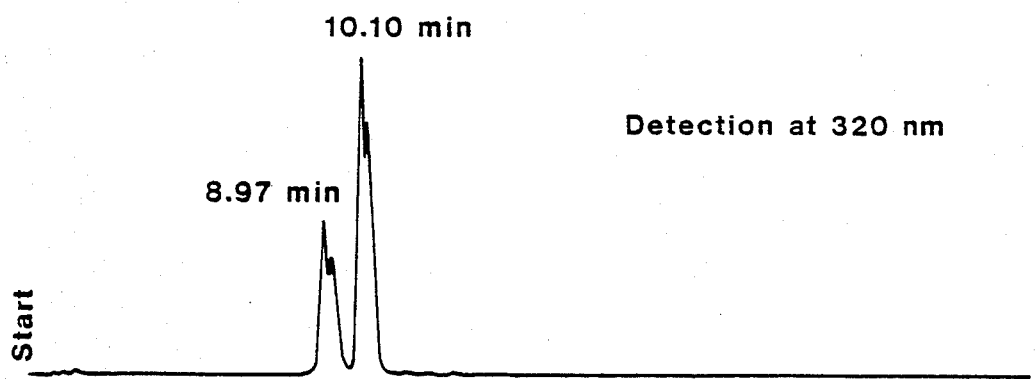

ANTIBIOTIC 273$a_1$

BACKGROUND OF THE INVENTION

Antibiotics paulomycin A and paulomycin B are disclosed in U.S. Pat. No. 4,335,108. These antibiotics are produced in a fermentation using *Streptomyces paulus*, strain 273,NRRL12251. Example 1 of U.S. Pat. No. 4,335,108 discloses the fermentation process and recovery of the desired antibiotics. Examples 2 and 3 disclose the isolation processes for preparing the essentially pure crystalline preparations of paulomycin A and paulomycin B, respectively.

BRIEF SUMMARY OF THE INVENTION

We have discovered a new and useful antibiotic entity in the fermentation broth disclosed in U.S. Pat. No. 4,335,108. Further, we have discovered a new fermentation which, advantageously, gives higher fermentation titers of the new antibiotic entity than is possible in the fermentation of U.S. Pat. No. 4,335,108. The new antibiotic entity has been designated 273$a_1$. This entity has been found to be a mixture which has been resolved into two antibiotic entities. These latter entities have been designated 273$a_1\alpha$, and 273$a_1\beta$.

Thus, disclosed and claimed herein, are three new and useful antibiotics. These compounds have the properties of adversely affecting the growth of Gram-positive bacteria, for example, *Bacillus subtilis, Staphylococcus aureus, Streptococcus pyogenes* and *Streptococcus faecalis*. Thus, they can be used alone or in combination with other antibacterial agents to prevent the growth of, or reduce the number of, such microorganisms present in various environments. Also, they are useful in wash solutions for sanitation purposes, as in the washing of hands and in the cleaning of equipment, floors, or furnishings of contaminated rooms or laboratories; they are also useful as an industrial preservative, for example, as a bacteriostatic rinse for laundered clothes and for impregnating papers and fabrics; and they are useful for suppressing the growth of sensitive organisms in plate assays and other microbiological media.

Antibiotic 273$a_1$ is, advantageously, more soluble in aqueous solutions than paulomycin thereby facilitating the formulation of the antibiotic. Paulomycin is relatively insoluble in water.

DETAILED DESCRIPTION OF THE INVENTION

Figure 1:
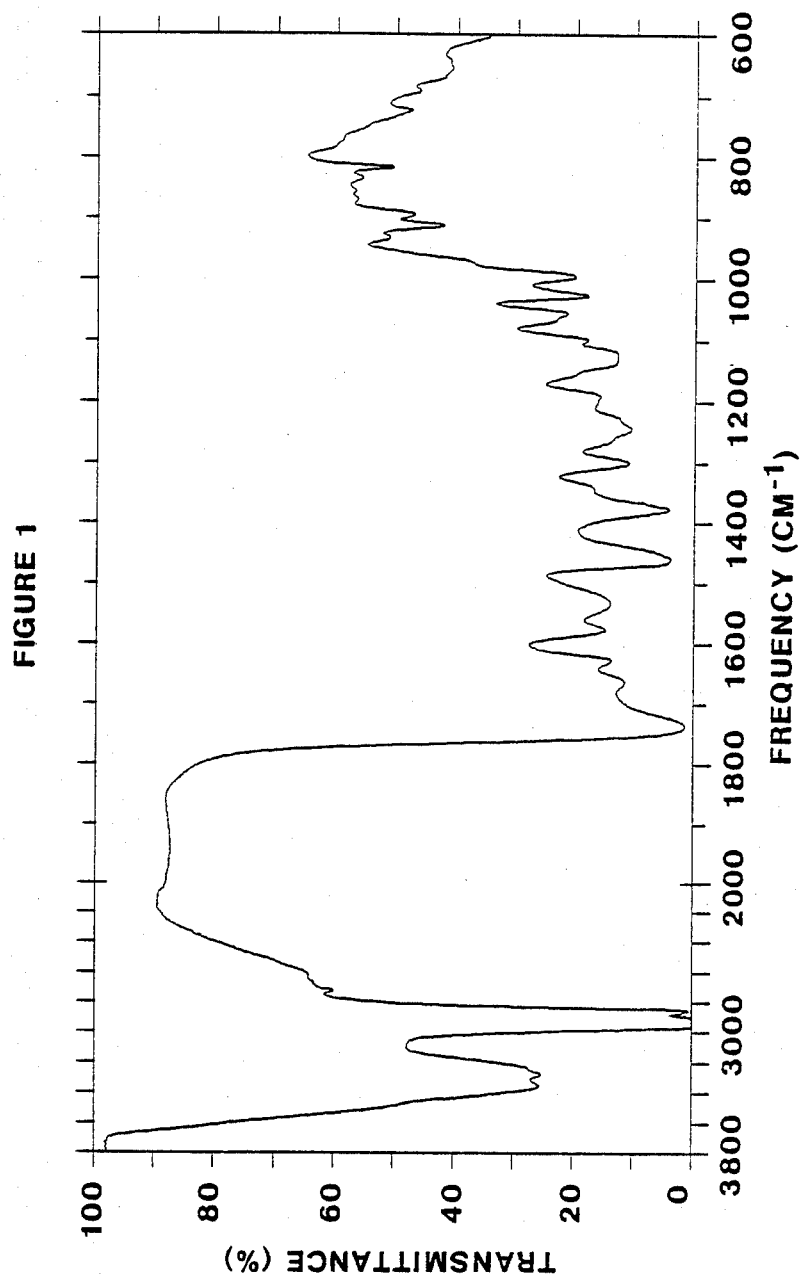

Chemical and Physical Propertes of the Antibiotics
Chemical and Physical Properties of Antibiotic 273$a_1$ Infrared Absorption Spectrum Antibiotic 273$a_1$ has a characteristic infrared absorption spectrum in mineral oil mull as shown in FIG. 1 of the drawings. Peaks are observed at the following wave lengths.

| Band Frequency[1] | Intensity[2] | | Band Frequency | Intensity | |
|---|---|---|---|---|---|
| 3476.6 | 49 | SH | 1244.0 | 11 | |
| 3348.4 | 26 | | 1230.5 | 12 | SH |
| 3272.2 | 25 | | 1191.0 | 16 | |
| 3239.4 | 27 | SH | 1120.6 | 13 | |
| 2958.7 | 0 | | 1098.4 | 17 | |
| 2867.1 | 2 | SH | 1055.0 | 21 | |
| 2853.6 | 1 | | 1026.1 | 18 | |
| 2728.3 | 60 | | 995.2 | 20 | |
| 2675.2 | 63 | SH | 973.0 | 37 | SH |
| 2631.8 | 64 | SH | 930.6 | 51 | |
| 2537.3 | 69 | SH | | | |
| 1946.1 | 87 | | 911.3 | 42 | |
| 1736.8 | 1 | | 893.0 | 47 | |
| 1662.6 | 11 | | 868.9 | 57 | |
| 1626.9 | 14 | | 855.4 | 57 | |
| 1575.8 | 15 | | 834.2 | 56 | |
| 1532.4 | 14 | | 816.8 | 50 | |
| 1457.2 | 3 | | 768.6 | 59 | SH |
| 1377.1 | 4 | | 722.3 | 47 | |
| 1344.3 | 17 | SH | 689.5 | 46 | |
| 1299.0 | 11 | | 651.9 | 41 | |
| 1260.4 | 14 | SH | | | |

[1]Wave numbers (Cm$^{-1}$)
[2]Percent transmittance (% T), sh = shoulder
Intensity at 3800 cm$^{-1}$ is 97% T.
Maximum % T = 98 at 3772.7 cm$^{-1}$.

Ultraviolet Absorption Spectrum

Figure 2:
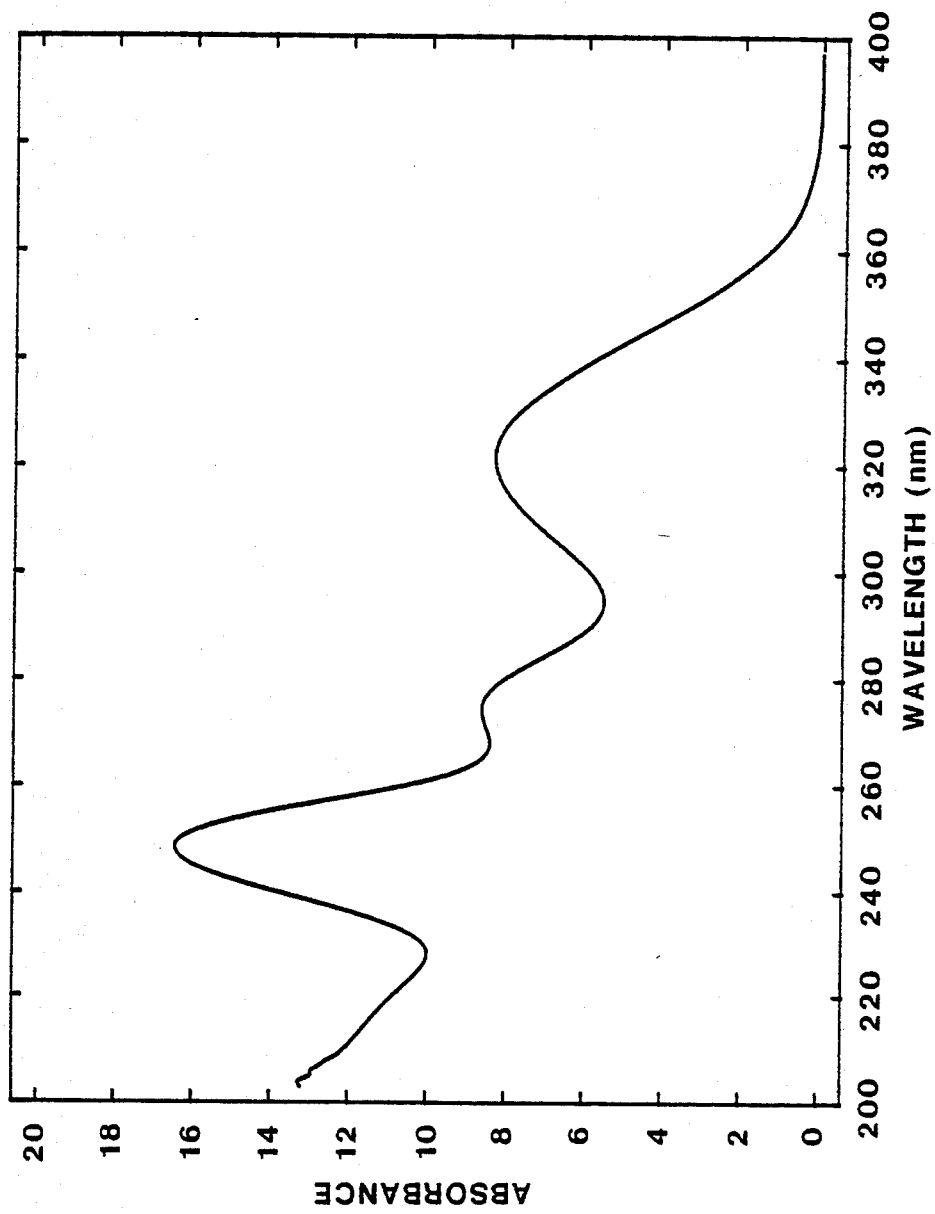

The UV spectrum of antibiotic 273$a_1$ is shown in FIG. 2 of the drawings. The solution of antibiotic in methanol displayed absorption as follows:

| λ max | (a) |
|---|---|
| 248 nm | 16.45 |
| 274 | 8.61 |
| 322 | 8.31 |

Proton Magnetic Resonance (1H-NMR) Spectrum

Figure 3:
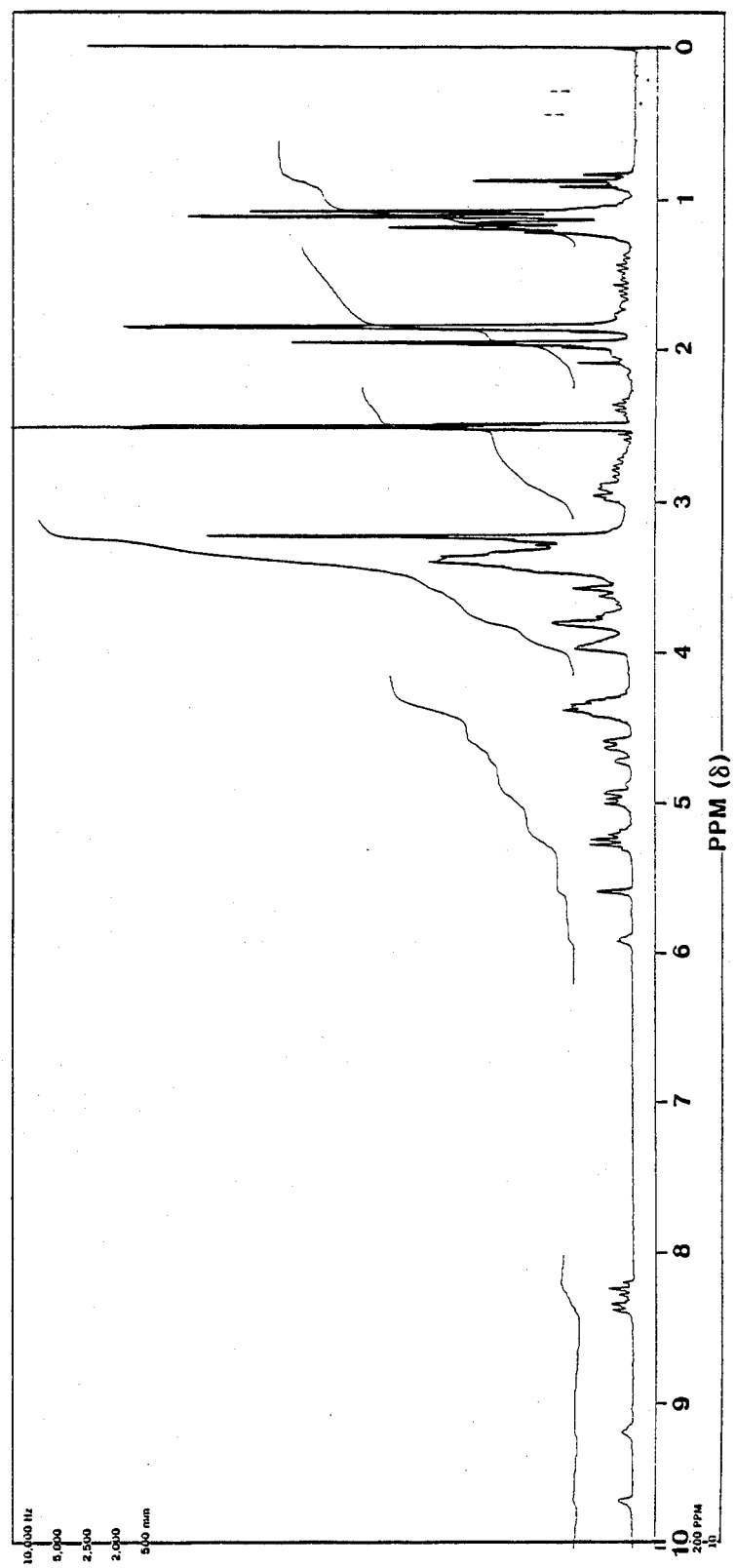

The $^1$-H-NMR spectrum of antibiotic 273$a_1$ at 200 MHZ is shown in FIG. 3 of the drawings. The $^1$H-NMR spectrum was observed on a Varian XL-100-15 Spectrometer on a solution (ca. 0.5 ml., ca. 150 mg/ml) of the sample of the antibiotic in deuterodimethylsulfoxide (d$_6$-DMSO). The spectrum was calibrated against internal tetramethylsilane and frequencies were recorded in ppm downfield from tetramethylsilane.

C-13 Nuclear Magnetic Resonance Spectrum

Figure 4:
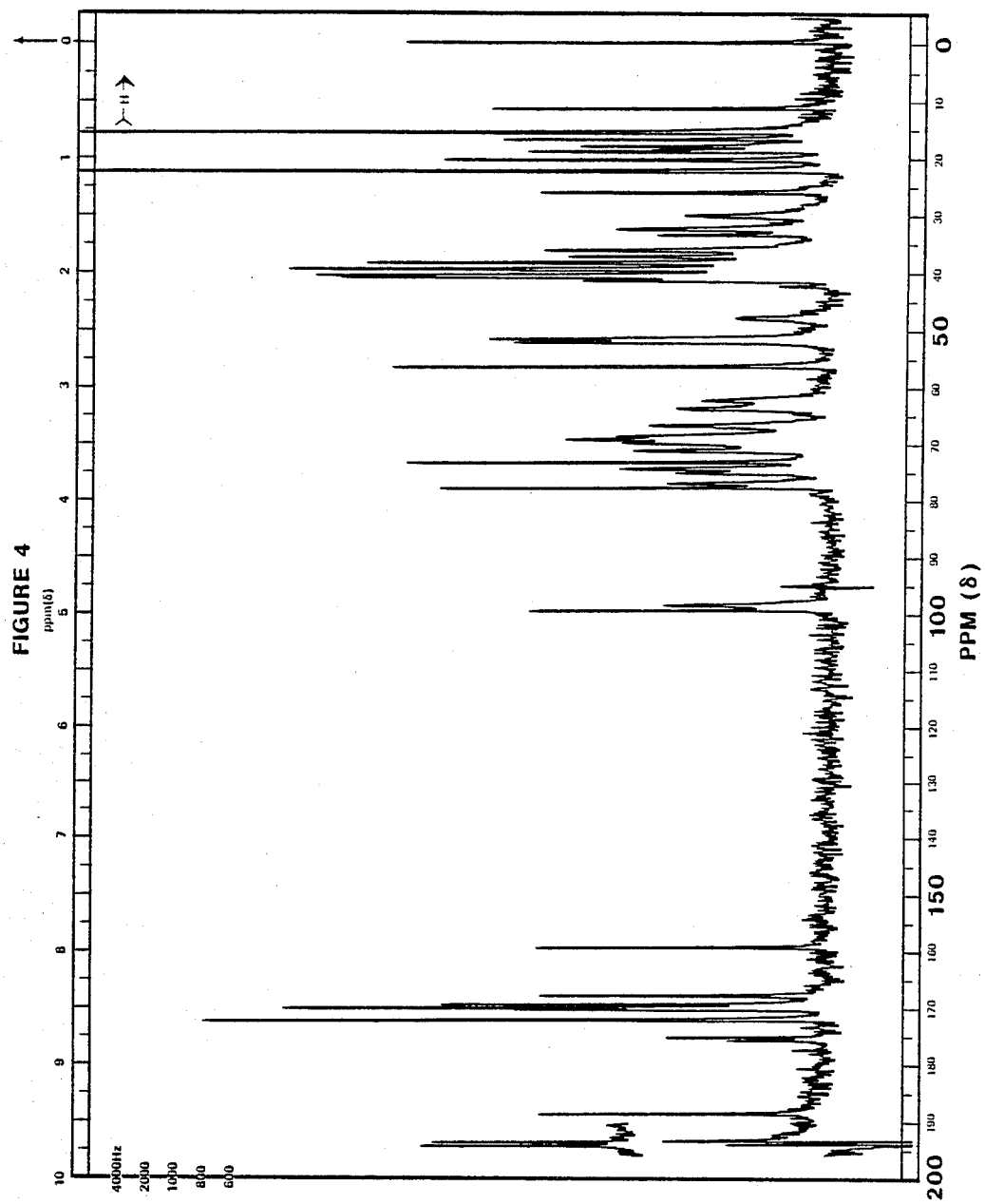

The C-13 NMR spectrum of antibiotic 273$a_1$ is shown in FIG. 4 of the drawings. The C-13 NMR spectrum was observed on a Varian CFT-80 Spectrometer operating at 20.0 MH$_3$ on a solution (ca. 0.5 ml., ca. 150 mg/ml) of the sample of the antibiotic in deuterodimethylsulfoxide (d$_6$-DMSO). The spectrum was calibrated against internal tetramethylsilane and frequencies were recorded in ppm downfield from tetramethylsilane.

Mass Spectrum

Figure 5:
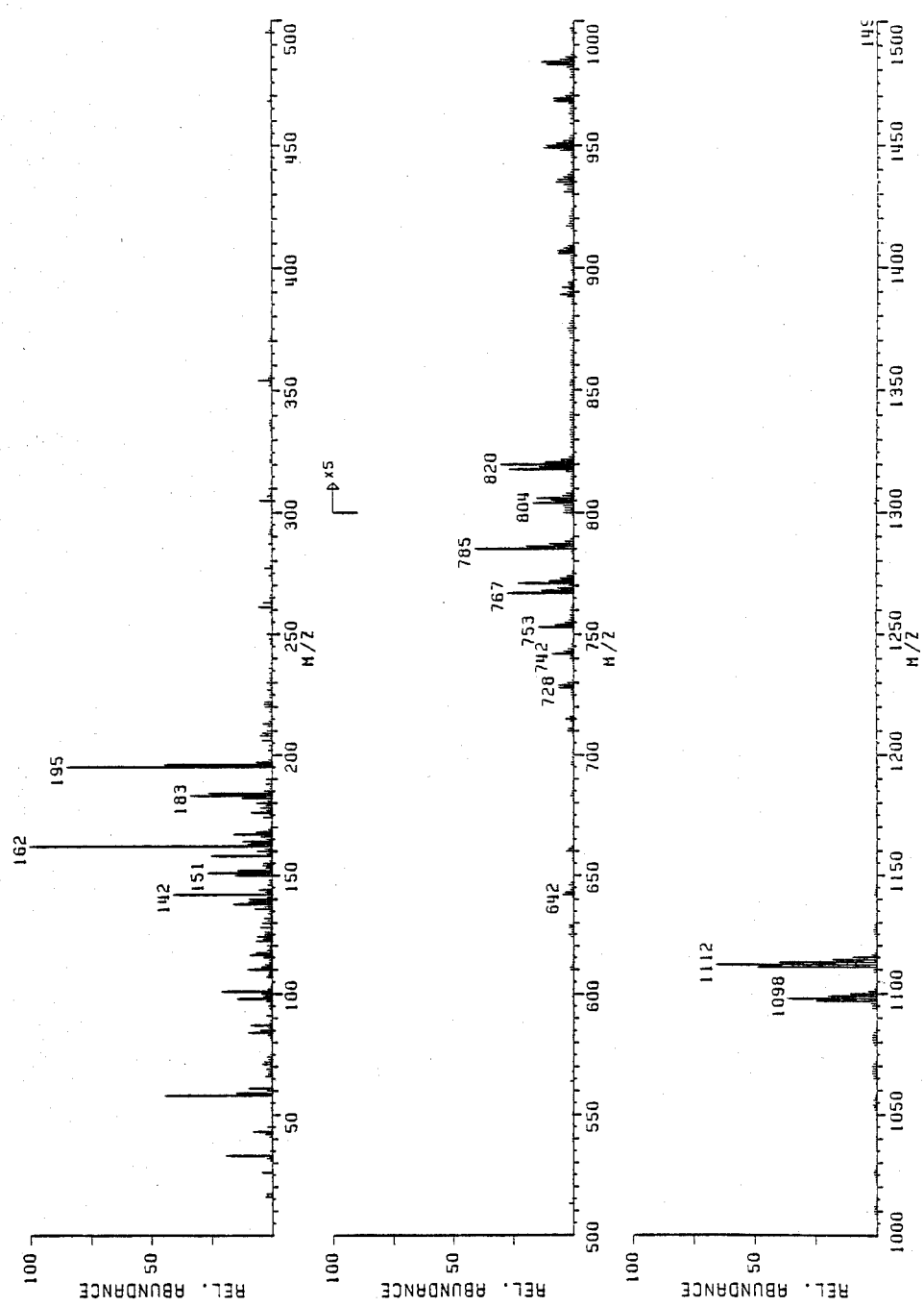

The mass spectrum of antibiotic 273$a_1$ is shown in FIG. 5 of the drawings. The mass spectrum was obtained on a ZAB-2F high resolution mass spectrometer using a fast atom bombardment (FAB) source. The spectrum shows that antibiotic 273$a_1$ is a mixture of two compounds with molecular weights of 1098 (273$a_1\beta$) and 1112 (273$a_1\alpha$).

HPLC Chromatography

HPLC chromatogram of antibiotic 273$a_1$ is presented in FIG. 6 of the drawings. The chromatogram shows the presence of two components in antibiotic 273$a_1$, antibiotic 273$a_1\alpha$ (retention time ca. 10.31 minutes) and antibiotic 273$a_1\beta$ (retention time ca. 9.81 minutes).

All HPLC chromatography was carried out on a Hewlett-Packard Model 1084B (Hewlett-Packard, Avondale, Calif.) instrument equipped with an HP model 79875A variable wave length detector and operating in the dual pump mode. A Brownless 10 cm×4.6 mm stainless steel column packaged with C$_{18}$ (10μ)

reverse phase was used. Mobile phases were prepared using Burdick and Jackson distilled in glass solvents. All samples and aqueous phases were filtered through a 0.45 micron filter. Mobile phase: A, 0.05M pH 5.5 phosphate buffer; B, acetonitrile. Gradient conditions, T=0 minutes, %B=15%; T=5 minutes, %B=15%; T=15 minutes, %B=40%. Samples were prepared as 1 mg/ml solutions in the initial mobile phase.

Thin Layer Chromatography

Figure 7:
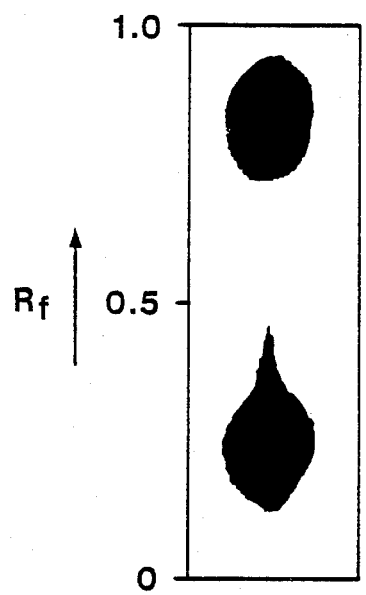

Bioautogram of antibiotic 273a$_1$ (Rf, 0.2) and paulomycin (Rf, 0.8) is presented in FIG. 7 of the drawings. Thin layer chromatograms were run on silica-gel G using chloroform-ethanol-water (25:30:5 v/v) as the mobile phase. Antibiotic 273a$_1$ was detected by bioautography on *Micrococcus luteus*-seeded trays.

Melting point: ca. 120° C. with decomposition.

Optical Rotation: $[\alpha]_D^{25}$, ~33° (C, 0.890, methanol).

Titration Data: Two titratable groups with pKa's of ca. 4.0–4.2. A third group had a pKa of ca. 7.5. Equivalent weight: first break, 576; second break, 376. Solvent, 60% aq. ethanol; titrant KOH.

Elemental Analysis: Calcd for a mixture of 60% 273a$_1\alpha$ and 40% 273a$_1\beta$: C, 47.24; H, 5.70; N, 5.06; S, 8.68. Found: C, 46.42; H, 5.68; N, 4.90; S, 8.73.

Appearance: Colorless amorphous acidic material.

Solubilities: Soluble in lower alcohols, ketones, ethyl acetate; less soluble in chloroform, methylene chloride; insoluble in ether and saturated hydrocarbon solvents. The free acid form is insoluble in water but soluble in phosphate buffer at physiological pH's (7.0–7.5). Salts are soluble in water.

Biological Properties of Antibiotic 273a$_1$

Antimicrobial Spectrum of Antibiotic 273a$_1$

Antibiotic 273a$_1$ is active against various Gram-positive bacteria as shown in the following table:

Assay

The antibacterial assay is a standard microplate agar assay using PYG agar, pH 6. PYG agar consists of the following ingredients:

| | |
|---|---|
| Peptone | 10 g./l. |
| Yeast extract | 5 g./l. |
| Glucose | 1 g./l. |
| Agar | 15 g./l. |
| Distilled water, q.s. | 1 l. |

The MIC is determined by standard methods. The inocula are overnight cultures of the test organisms, diluted so that the final population contains approximately 10$^5$ cells/ml. The agar plates are incubated at 28° to 37° C. for 24 hours. The lowest antibiotic concentration which allows no growth=MIC or minimum inhibitory concentration.

| | Miniumum Inhibitory Concentration | |
|---|---|---|
| Organism | UC # | (mcg/ml) |
| *Staphylococcus aureus* | 76 | <0.16 |
| *Staphylococcus aureus* | 6685 | <0.16 |
| *Staphylococcus aureus* | 6690 | <0.16 |
| *Streptococcus pyogenes* | 152 | <0.16 |
| *Streptococcus faecalis* | 694 | 0.62 |
| *Streptococcus pneumoniae* | 41 | <0.16 |
| *Escherichia coli* | 45 | >160 |
| *Klebsiella pneumoniae* | 58 | >160 |
| *Salmonella schottmuelleri* | 126 | >160 |

| | Miniumum Inhibitory Concentration | |
|---|---|---|
| Organism | UC # | (mcg/ml) |
| *Pseudomonas aeruginosa* | 95 | >160 |

"UC" is a registered trademark of the Upjohn Company Culture Collection.

Chemical and Physical Properties of Antibiotic 273a$_1\alpha$

Figure 8:
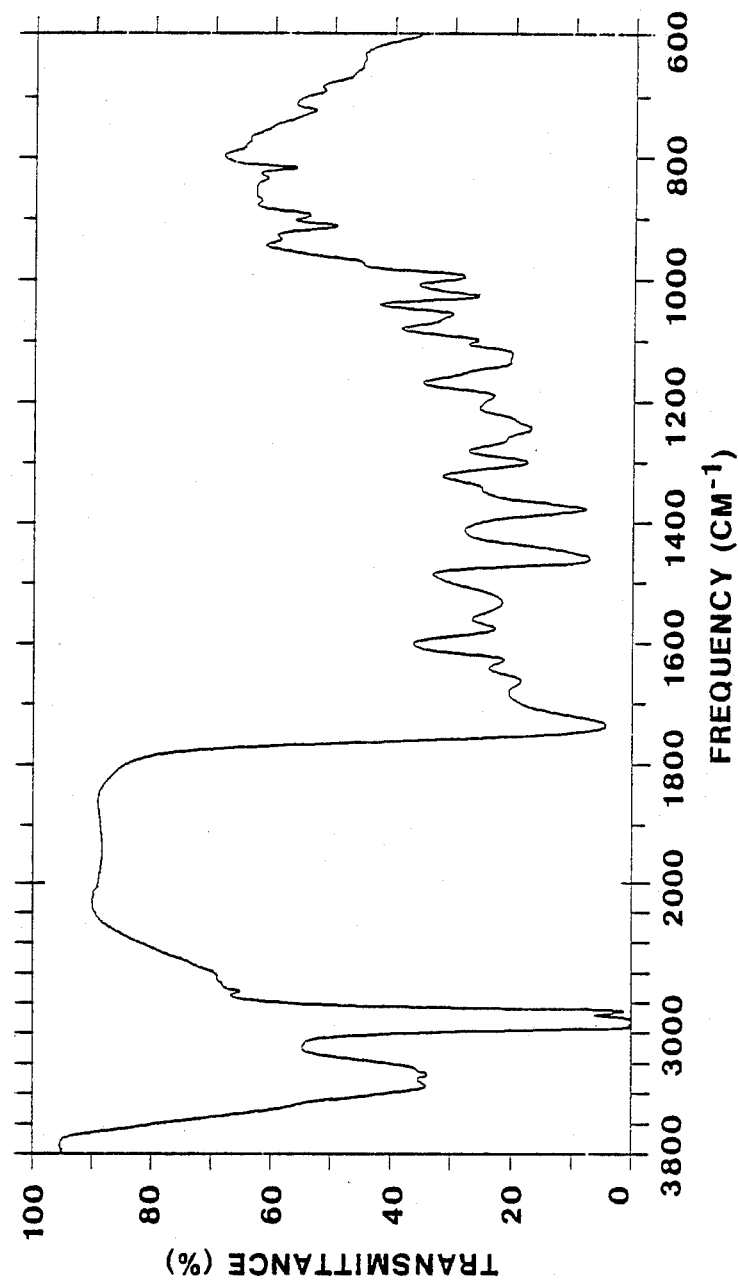

Infrared Absorption Spectrum:

Antibiotic 273a$_1\alpha$ has a characteristic infrared spectrum in mineral oil mull as shown in FIG. 8 of the drawings. Peaks are observed at the following wave lengths:

| Band Frequency[1] | Intensity[2] | | Band Frequency[1] | Intensity[2] | |
|---|---|---|---|---|---|
| 3469.9 | 55 | SH | 1261.4 | 21 | SH |
| 3351.3 | 34 | | 1243.1 | 17 | |
| 3272.2 | 34 | | 1190.0 | 23 | |
| 3238.4 | 36 | SH | 1120.6 | 20 | |
| 2952.0 | 0 | | 1098.4 | 25 | |
| 2913.4 | 0 | | 1056.0 | 29 | |
| 2868.1 | 3 | SH | 1026.1 | 25 | |
| 2854.6 | 1 | | 994.3 | 28 | |
| 2724.4 | 65 | | 975.0 | 44 | SH |
| 1949.0 | 88 | | | | |
| 1735.9 | 4 | | 932.5 | 59 | |
| 1661.6 | 19 | | 911.3 | 49 | |
| 1626.9 | 21 | | 894.0 | 54 | |
| 1574.8 | 23 | | 872.7 | 62 | SH |
| 1532.4 | 22 | | 833.2 | 61 | |
| 1460.1 | 7 | | 816.8 | 56 | |
| 1377.1 | 7 | | 768.6 | 64 | SH |
| 1343.4 | 25 | SH | 722.3 | 53 | |
| 1299.0 | 18 | | 689.5 | 52 | |

[1]Wave numbers (cm$^{-1}$).
[2]Percent transmittance (% T), sh = shoulder.
Intensity at 3800 cm$^{-1}$ is 95%.
Maximum % T: 95 at 3746 cm$^{-1}$.

Figure 9:
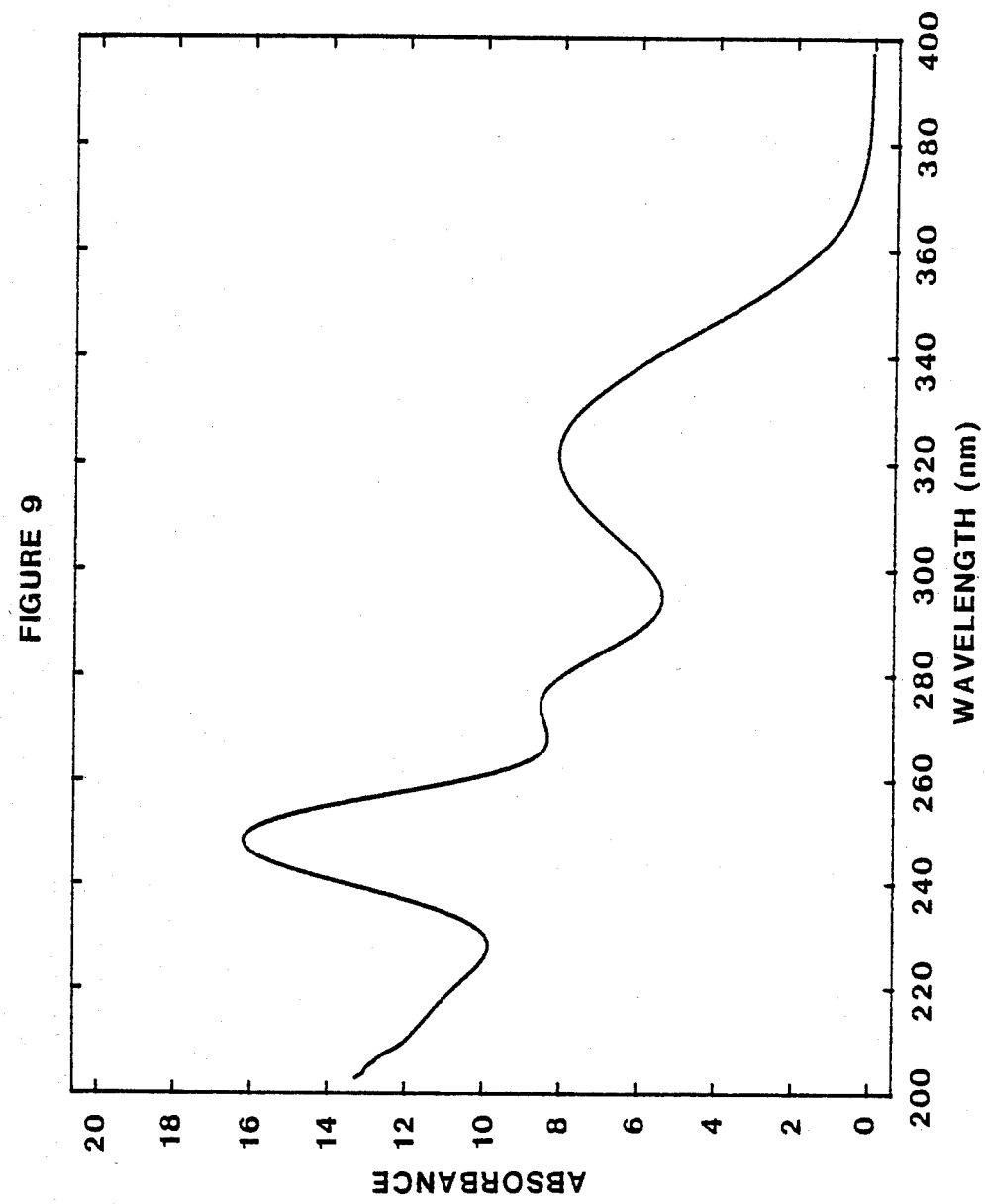

Ultraviolet Absorption Spectrum:

The UV spectrum of antibiotic 273a$_1\alpha$ is shown in FIG. 9 of the drawings. The solution of the antibiotic in methanol displayed absorption as follows:

| λ max | (a) |
|---|---|
| 248 nm | 16.20 |
| 274 | 8.51 |
| 321 | 8.09 |

Figure 10:
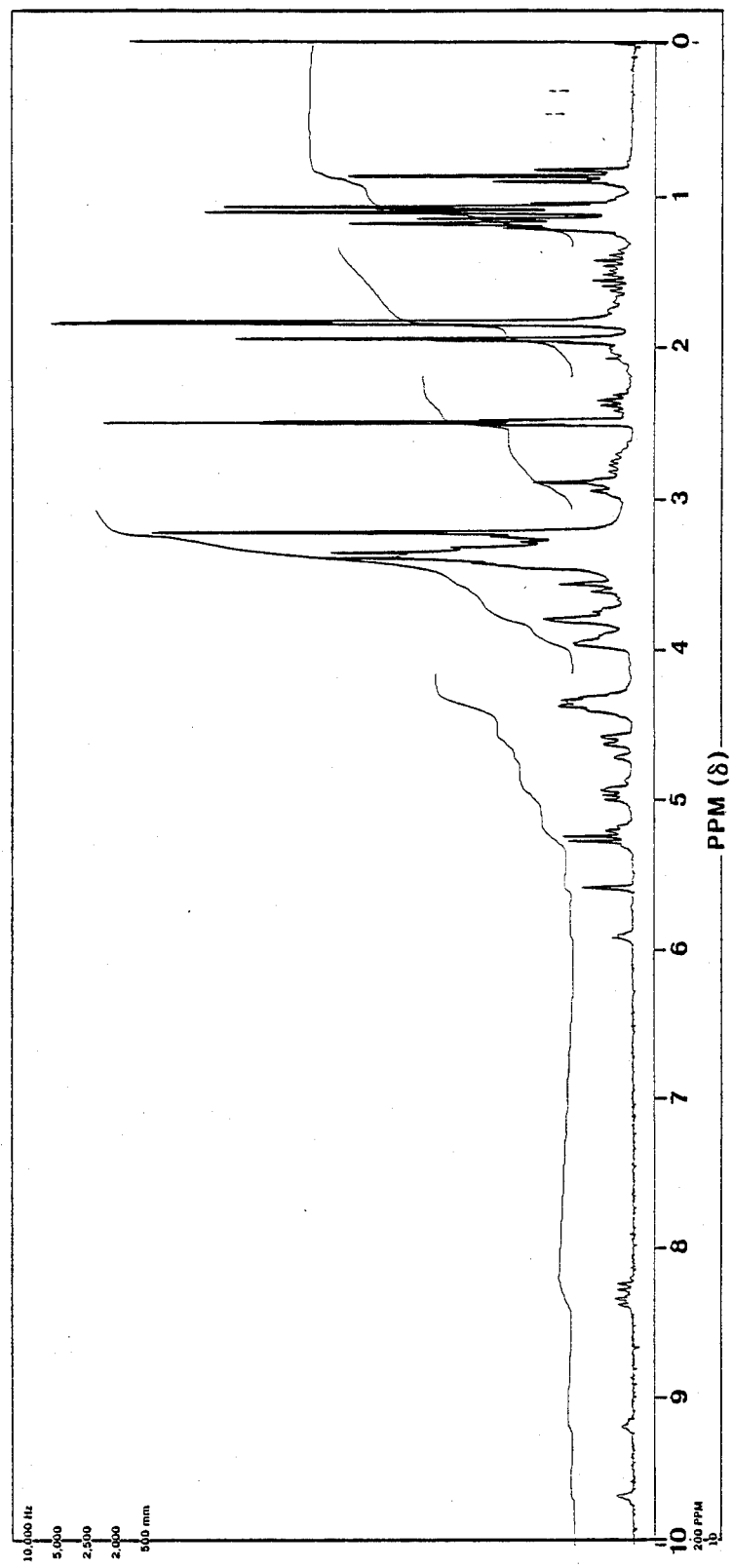

Proton Magnetic Resonance ($^1$H-NMR) Spectrum:

The $^1$H-NMR spectrum of antibiotic 273a$_1\alpha$ at 200 MHZ is shown in FIG. 10 of the drawings. The $^1$H-NMR spectrum was observed as described above.

Figure 11:
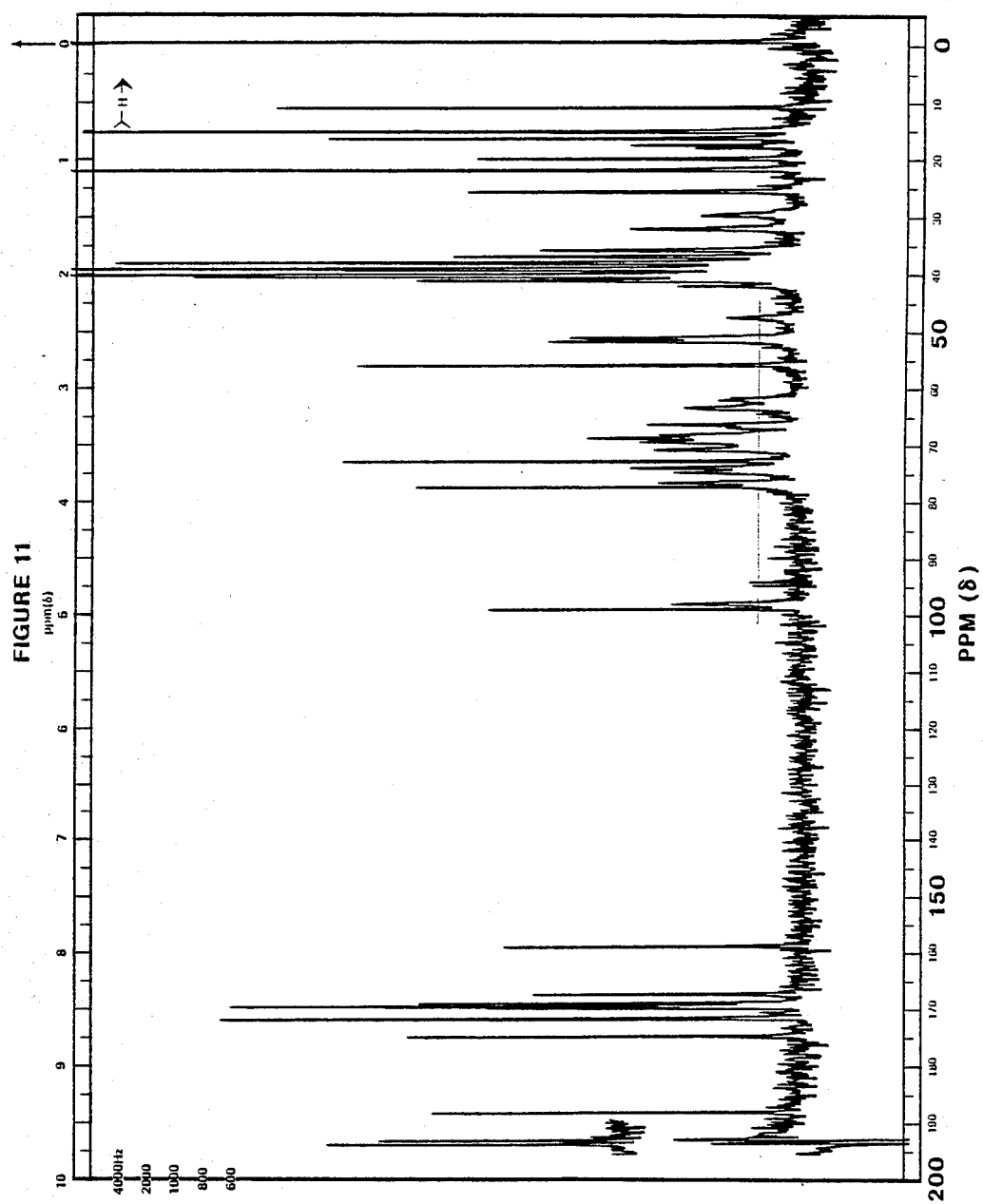

C-13 Nuclear Magnetic Resonance Spectrum:

The C-13 NMR spectrum of antibiotic 273a$_1\alpha$ is shown in FIG. 11 of the drawings. The C-13 NMR spectrum was observed as described above.

Figure 12:
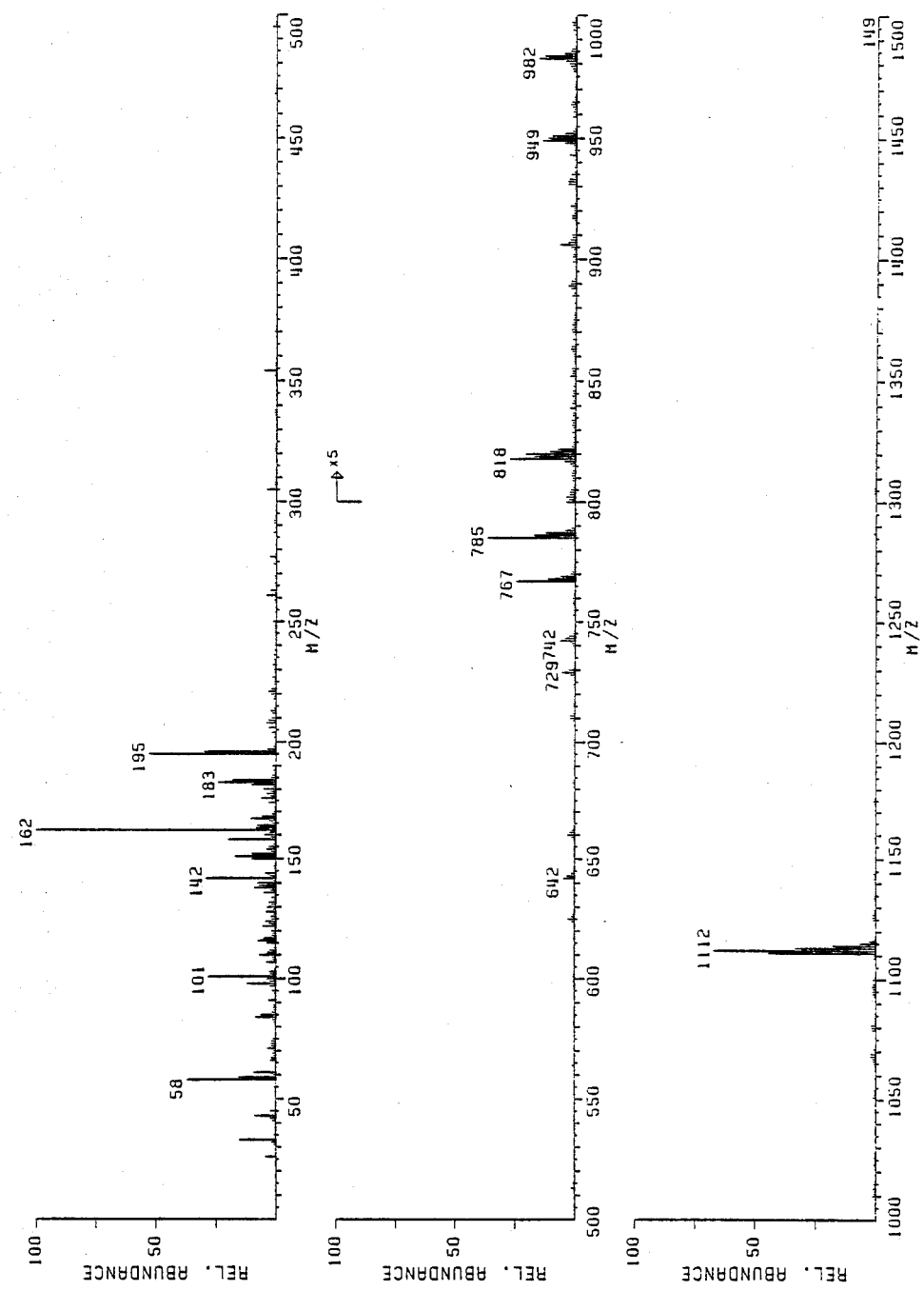

Mass Spectrum:

The mass spectrum of antibiotic 273a$_1\alpha$ is shown in FIG. 12 of the drawings. The mass spectrum was obtained on a ZAB-2F high resolution mass spectrometer using a fast atom bombardment (FAB) source.

Figure 13:
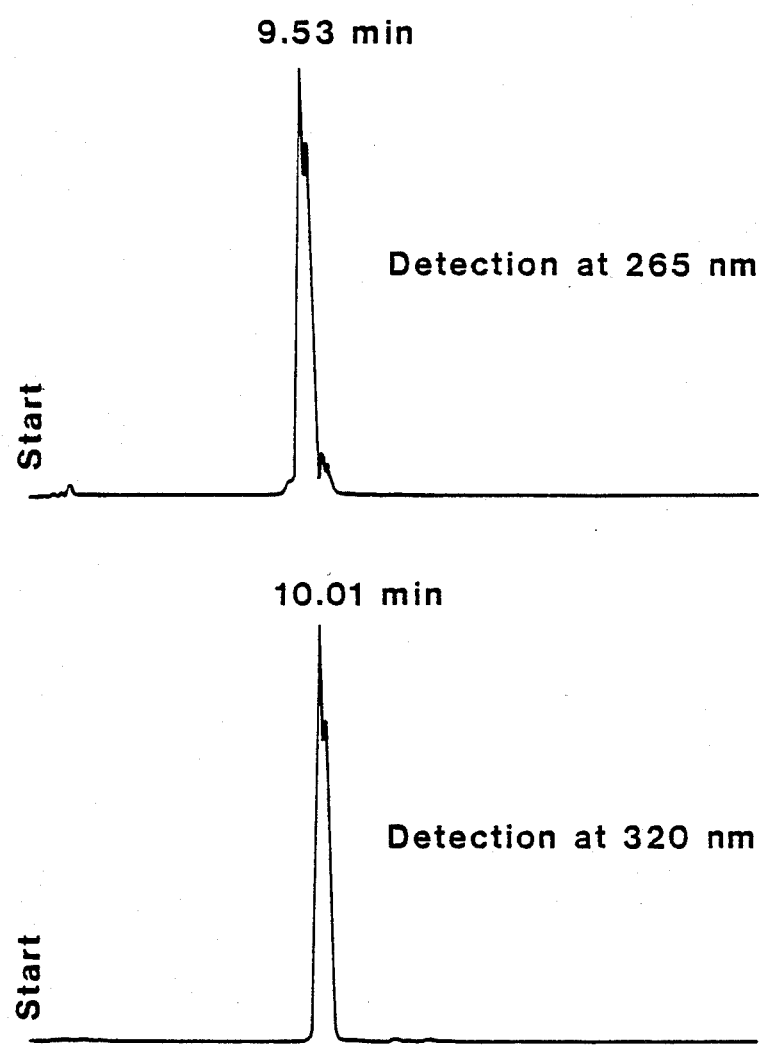

HPLC Chromatography:

HPLC chromatogram of antibiotic 273a$_1\alpha$ is presented in FIG. 13 of the drawings. The chromatogram shows the presence of antibiotic 273a$_1$a (retention time ca. 10.01 minutes).

The HPLC chromatography was carried out as described above.

Melting Point: ca. 120° C. (decomposition).

Optical Rotation: $[\alpha]_D^{25} -31°$ (C, 0.905, methanol).

Titration Data: Two titratable groups with pKa's of ca. 4.0–4.2. A third group had pKa of ca. 7.5. Equivalent weight: first break, 577; second break, 379. Solvent, 60% aqueous ethanol; titrant KOH.

Elemental Analyses: Calcd for $C_{44}H_{64}N_4O_{23}S_3$: C, 47.48; H, 5.75; N, 5.03; S, 8.63. Found: C, 46.82; H, 5.78; N, 4.93; S, 8.72.

Molecular Weight: Calcd, 1112. Found by FAB/MS 1112.

Appearance: Colorless amorphous acidic material.

Solubilities: Soluble in lower alcohols, ketones, ethyl acetate; less soluble in chloroform, methylene chloride; insoluble in ether and saturated hydrocarbon solvents. The free acid form is insoluble in water, but soluble in phosphate buffers at physiological pH (7.0–7.5). Salts are soluble in water.

Biological Properties of Antibiotic 273a$_1\alpha$

Antibiotic 273a$_1\alpha$ is active against various Gram-positive bacteria including several *Staphylococcus aureus* strains resistant to other antibiotics as shown in the following table.

Assay

The antibacterial assay is as described above for antibiotic 273a$_1$.

| Organism | UC # | Minimum Inhibitory Concentration (mcg/ml) |
|---|---|---|
| *Staphylococcus aureus* | 76 | <0.04 |
| *Staphylococcus aureus* | 3444 | <0.04 |
| *Staphylococcus aureus* | 3445 | <0.04 |
| *Staphylococcus aureus* | 6685 | <0.04 |
| *Staphylococcus aureus* | 6688 | <0.04 |
| *Staphylococcus aureus* | 6694 | <0.04 |
| *Staphylococcus aureus* | 6695 | 0.08 |
| *Staphylococcus aureus* | 9210 | 0.08 |
| *Staphylococcus aureus* | 9212 | 0.08 |
| *Staphylococcus aureus* | 9213 | <0.04 |
| *Staphylococcus aureus* | 9215 | <0.04 |
| *Staphylococcus aureus* | 9216 | <0.04 |

Chemical and Physical Properties of Antibiotic 273a$_1\beta$

Figure 14:
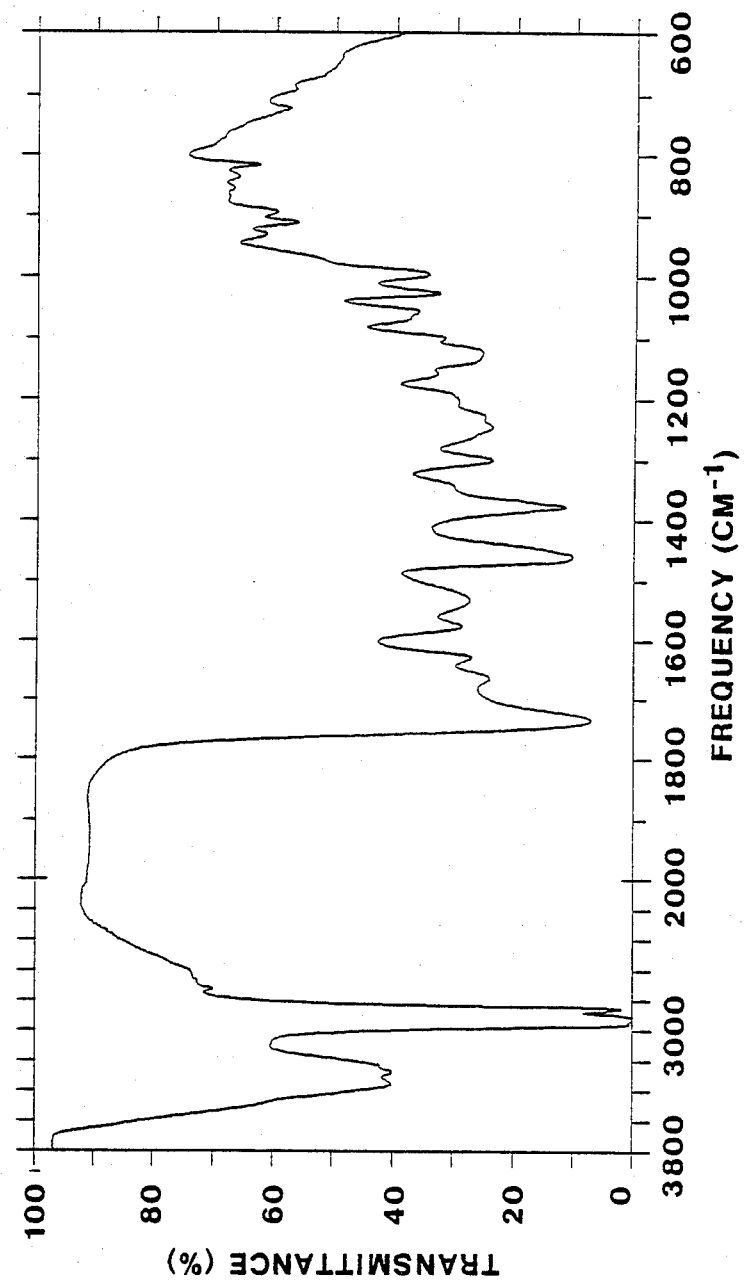

Infrared Absorption Spectrum:

Antibiotic 273a$_1\beta$ has a characteristic infrared spectrum in mineral oil mull as shown in FIG. 14 of the drawings. Peaks are observed at the following wave lengths:

| Band Frequency[1] | Intensity[2] | | Band Frequency[1] | Intensity[2] | |
|---|---|---|---|---|---|
| 3466.0 | 60 | SH | 1227.6 | 25 | |
| 3350.3 | 40 | | 1202.6 | 29 | |
| 3273.1 | 40 | | 1156.3 | 33 | |
| 3237.5 | 42 | SH | 1122.5 | 26 | |
| 2953.9 | 0 | | 1099.4 | 31 | |
| 2915.3 | 0 | | 1064.7 | 37 | SH |
| 2868.1 | 4 | SH | 1055.0 | 36 | |
| 2854.6 | 2 | | 1026.1 | 32 | |
| 2725.4 | 70 | | 995.2 | 34 | |
| 1925.9 | 91 | | 973.0 | 52 | SH |
| 1735.9 | 7 | | 929.6 | 62 | |
| 1661.6 | 24 | | 910.3 | 56 | |
| 1627.9 | 27 | | 893.0 | 60 | |
| 1574.8 | 29 | | 854.4 | 67 | |
| 1530.5 | 27 | | 836.1 | 66 | |
| 1458.1 | 10 | | 816.8 | 63 | |
| 1377.1 | 11 | | 767.6 | 68 | SH |
| 1345.3 | 30 | SH | 722.3 | 57 | |
| 1300.0 | 23 | | 689.5 | 57 | |
| 1245.0 | 24 | | | | |

[1]Wave numbers (cm$^{-1}$).
[2]Percent transmittance (% T), sh = shoulder.
Intensity at 3800 cm$^{-1}$, 96.
Maximum % T: 97 at 3772 cm$^{-1}$.

Figure 15:
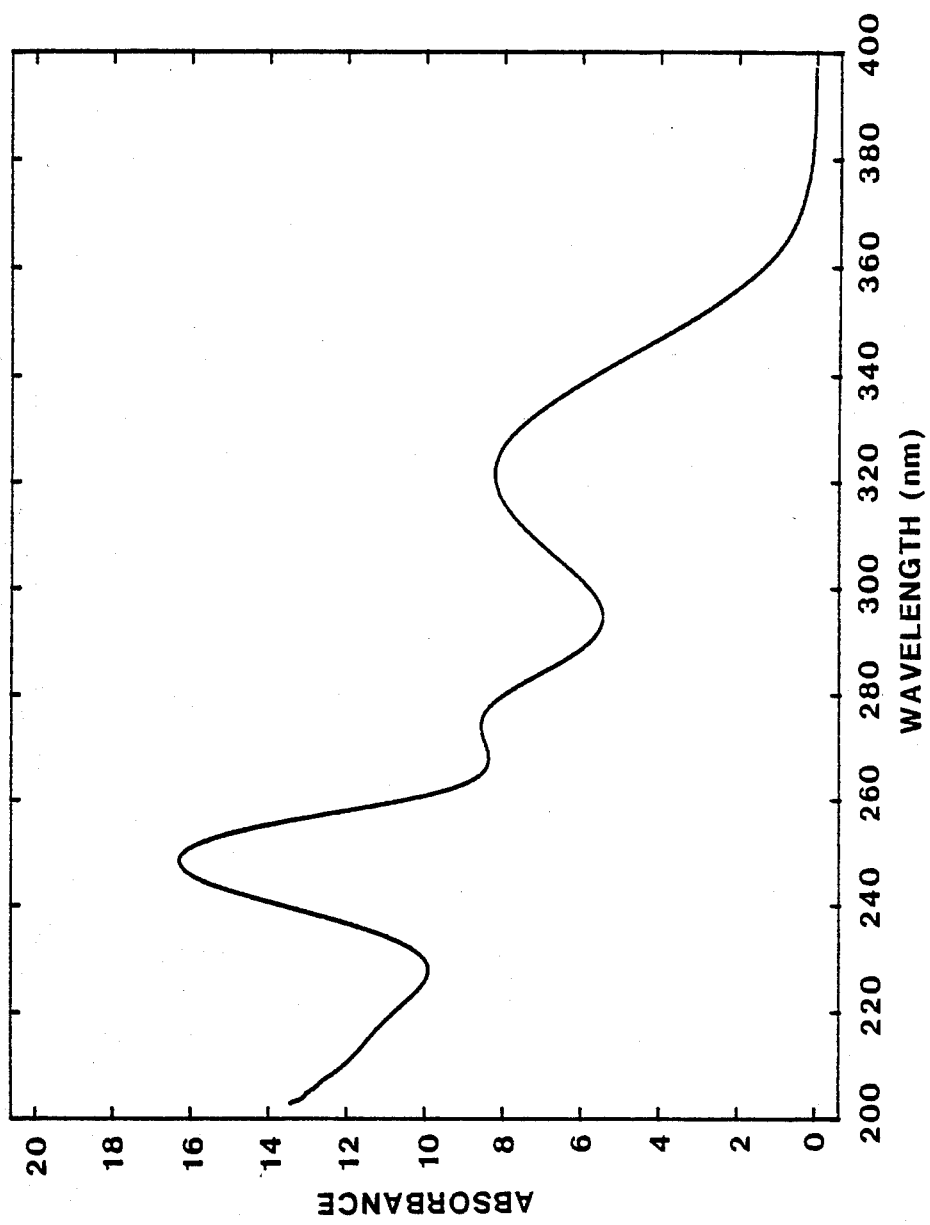

Ultraviolet Absorption Spectrum:

The U.V. spectrum of antibiotic 273a$_1\beta$ is shown in FIG. 15 of the drawings. The solution of the antibiotic is methanol displayed adsorptions as follows:

| λ max | (a) |
|---|---|
| 248 | 16.29 |
| 274 | 8.56 |
| 321 | 8.21 |

Figure 16:
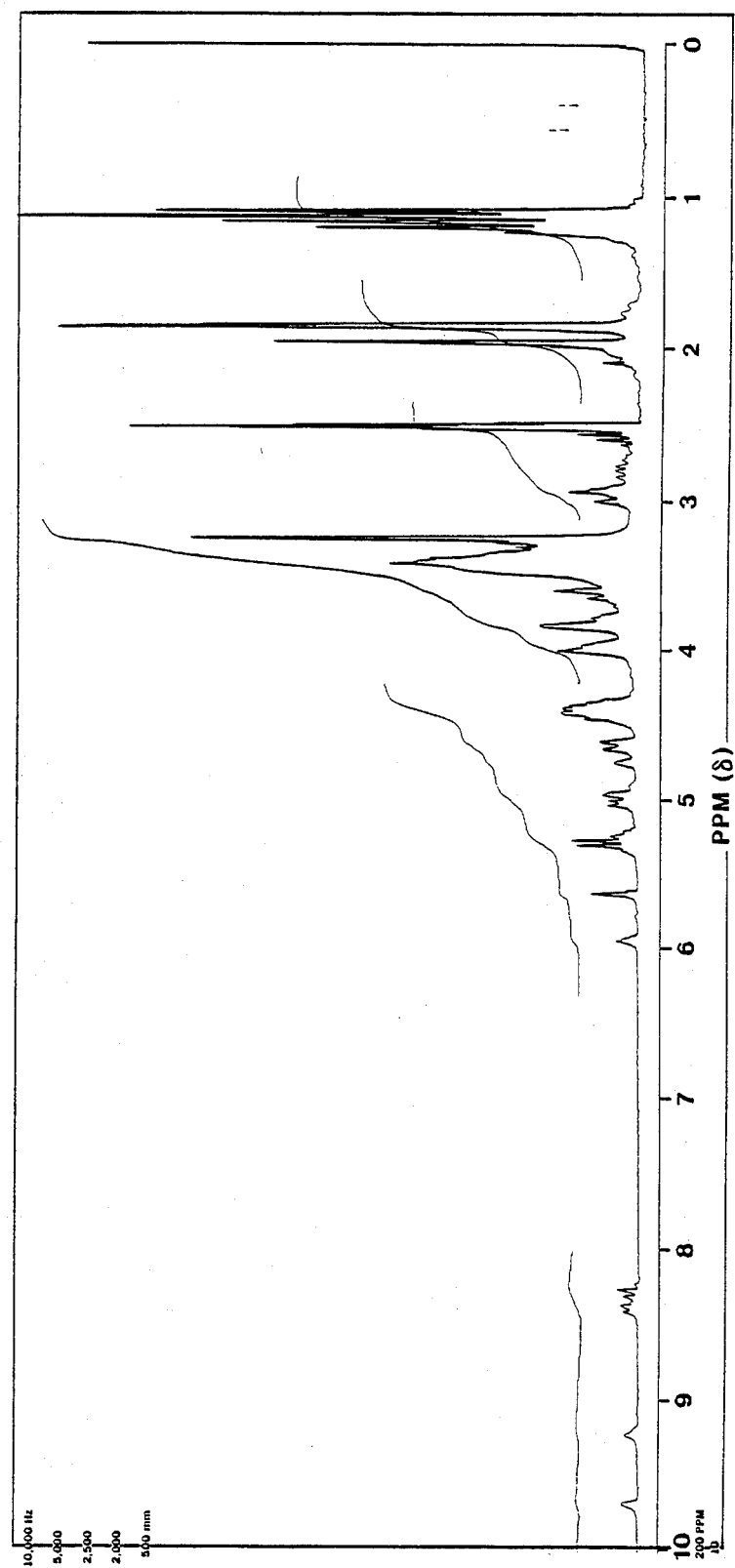

Proton Magnetic Resonance ($^1$H-NMR) Spectrum:

The $^1$-H-NMR spectrum of antibiotic 273a$_1\beta$ at 200 MHZ is shown in FIG. 16 of the drawings. The $^1$H-NMR spectrum was run as described previously.

Figure 17:
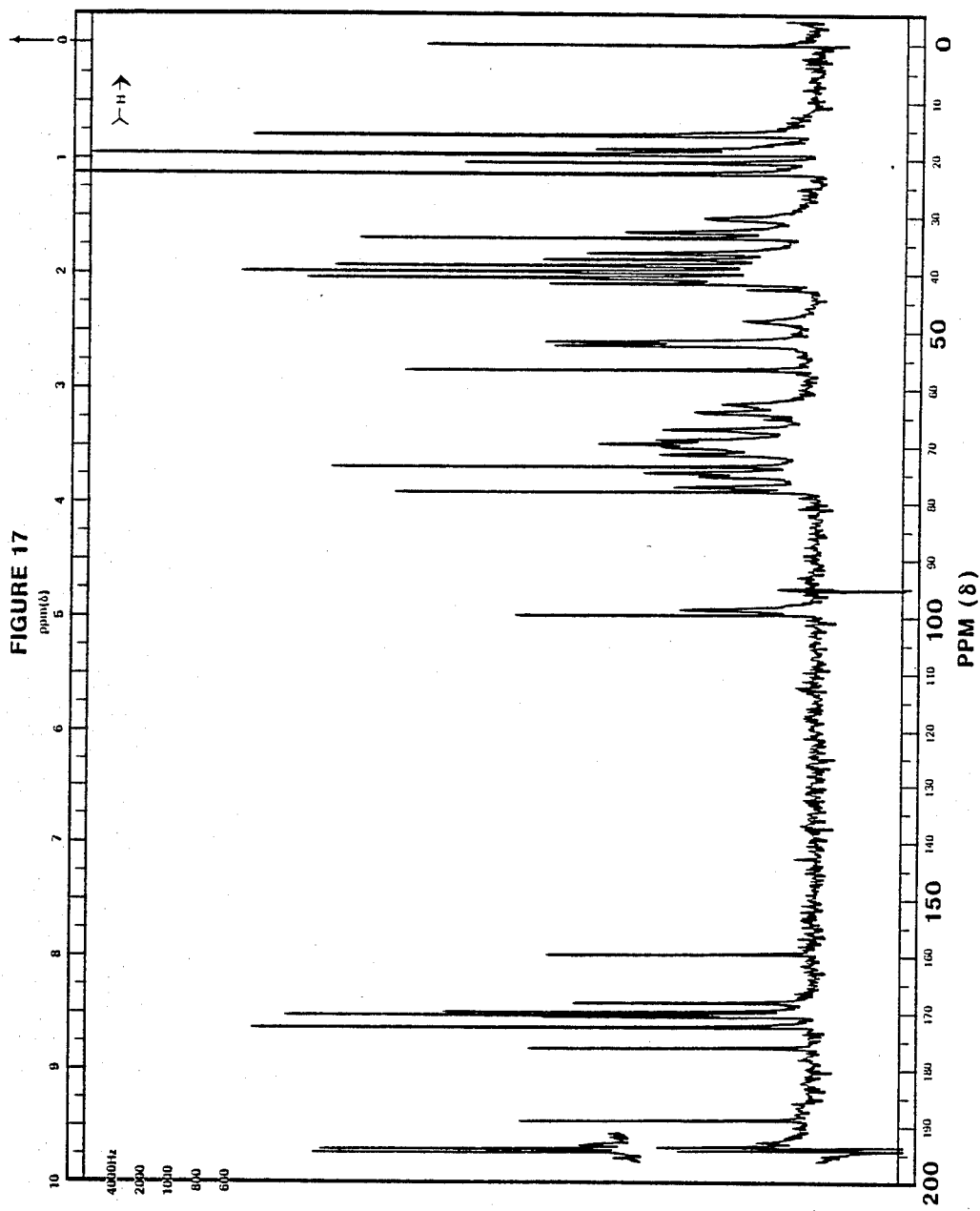

C-13 Nuclear Magnetic Resonance Spectrum:

The C-13 NMR spectrum of antibiotic 273a$_1\beta$ is shown in FIG. 17 of the drawings. The C-13 NMR spectrum was run as described previously.

Figure 18:
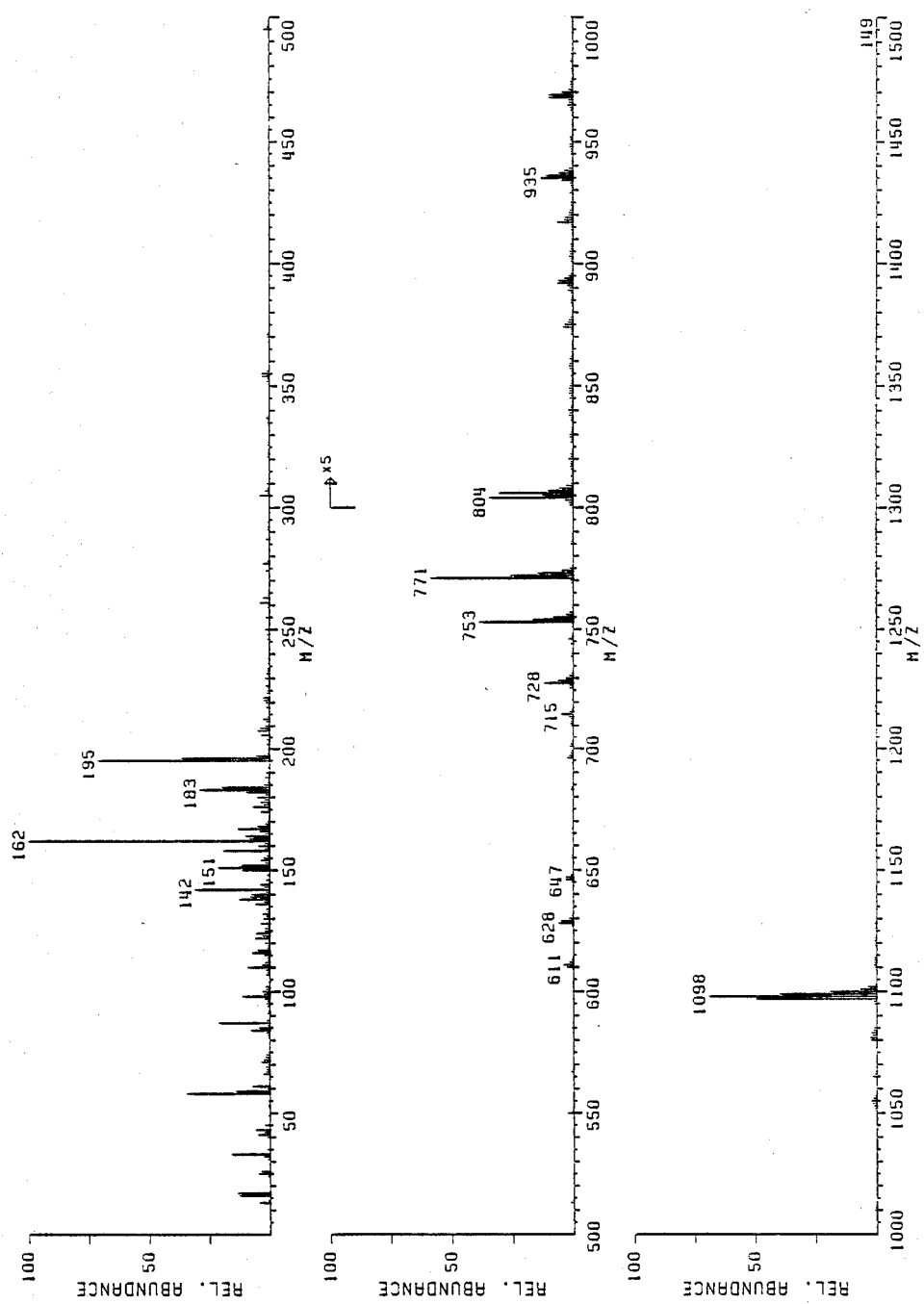

Mass Spectrum:

The mass spectrum of antibiotic 273a$_1\beta$ is shown in FIG. 18 of the drawings. The mass spectrum was obtained as described previously.

Figure 19:
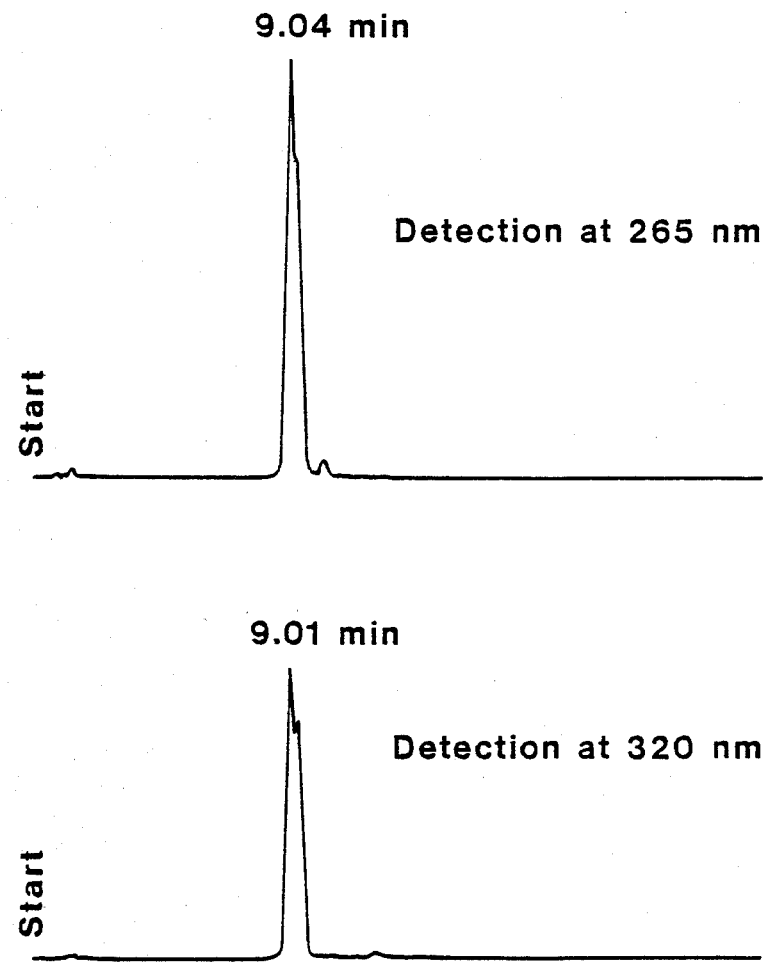

HPLC Chromatography:

HPLC chromatogram of antibiotic 273a$_1\beta$ is presented in FIG. 19 of the drawings. The chromatogram shows the presence of antibiotic 273a$_1\beta$ (retention time ca. 9.01 minutes).

The HPLC chromatography was carried out as described above.

Melting Point: ca. 120° C. (decomposition).

Optical Rotation: $[\alpha]_D^{25}$, $-35°$ (C, 0.908, methanol).

Titration Data: Two titratable groups with pKa's of ca. 4.0–4.2. A third group had pKa of ca. 7.5. Equivalent weight: First break, 577; second break, 379. Solvent 60% aqueous ethanol; titrant KOH.

Elemental Analyses: Calcd for $C_{43}H_{62}N_4O_{23}S_3 = $ C, 46.99; H, 5.64; N, 5.10; S, 8.74. Found: C, 46.22; H, 5.69; N, 5.00; S, 8.83.

Molecular Weight: Calcd., 1098. Found by FAB-MS, 1098.

Appearance: Colorless amorphous acidic material.

Solubilities: Soluble in lower alcohols, ketones, ethyl acetate, less soluble in chloroform, methylene chloride; insoluble in ether and saturated hydrocarbon solvents. The free acid form is insoluble in water but soluble in phosphate buffer at physiological pH's (7.0–7.5). Salts are soluble in water.

Biological Properties of Antibiotic 273a$_1\beta$

Antibiotic 273a$_1\beta$ is active against various Gram-positive bacteria including several *Staphylococcus aureus* strains resistant to other antibiotics as shown in the following table.

Assay

The antibacterial assay is a standard microplate agar assay as described above.

| Organism | UC | Minimum Inhibitory Concentration (mcg/ml) |
|---|---|---|
| Staphylococcus aureus | 76 | <0.04 |
| Staphylococcus aureus | 3444 | <0.04 |
| Staphylococcus aureus | 3445 | <0.04 |
| Staphylococcus aureus | 6685 | 0.08 |
| Staphylococcus aureus | 6688 | 0.08 |
| Staphylococcus aureus | 6694 | 0.08 |
| Staphylococcus aureus | 6695 | 0.16 |
| Staphylococcus aureus | 9210 | 0.08 |
| Staphylococcus aureus | 9212 | 0.08 |
| Staphylococcus aureus | 9213 | 0.08 |
| Staphylococcus aureus | 9215 | 0.08 |
| Staphylococcus aureus | 9216 | 0.08 |

REFERENCE TO THE DRAWINGS

FIG. 1: Infrared Abosrption Spectrum of Antibiotic 273a$_1$ in a Mineral Oil Mull.

FIG. 2: Ultraviolet Absorption Spectrum of Antibiotic 273a$_1$.

FIG. 3: Proton Magnetic Resonance Spectrum of Antibiotic 273a$_1$.

FIG. 4: C-13 Nuclear Magnetic Resonance Spectrum of Antibiotic 273a$_1$.

FIG. 5: Mass Spectrum of Antibiotic 273a$_1$.

FIG. 6: HPLC Chromatography of Antibiotic 273a$_1$.

FIG. 7: Thin Layer Chromatographic Comparison of Antibiotic 273a$_1$ and Paulomycin.

FIG. 8: Infrared Absorption Spectrum of Antibiotic 273a$_1\alpha$ in a Mineral Oil Mull.

FIG. 9: Ultraviolet Absorption Spectrum of Antibiotic 273a$_1\alpha$.

FIG. 10: Proton Magnetic Resonance Spectrum of Antibiotic 273a$_1\alpha$.

FIG. 11: C-13 Nuclear Magnetic Resonance Spectrum of Antibiotic 273a$_1\alpha$.

FIG. 12: Mass Spectrum of Antibiotic 273a$_1\alpha$.

FIG. 13: HPLC Chromatography of Antibiotic 273a$_1\alpha$.

FIG. 14: Infrared Absorption Spectrum of Antibiotic 273a$_1\beta$ in a Mineral Oil Mull.

FIG. 15: Ultraviolet Absorption Spectrum of Antibiotic 273a$_1\beta$.

FIG. 16: Proton Magnetic Resonance Spectrum of Antibiotic 273a$_1\beta$.

FIG. 17: C-13 Nuclear Magnetic Resonance Spectrum of Antibiotic 273a$_1\beta$.

FIG. 18: Mass Spectrum of Antibiotic 273a$_1\beta$.

FIG. 19: HPLC Chromatography of Antibiotic 273a$_1\beta$.

Antibiotic 273a$_1$ can be prepared by the process disclosed in U.S. Pat. No. 4,335,108, and modifications of said process disclosed in said patent. A preferred process for preparing antibiotic 273a$_1$ is disclosed herein in Example 1.

A variety of procedures can be employed in the isolation and purification of the compound of the subject invention from fermentation beers, for example, solvent extraction, partition chromatography, silica gel chromatography, liquid-liquid distribution in a Craig apparatus, and precipitation from solvents.

In a preferred recovery process the compound of the subject invention is recovered from its culture medium by separation of the mycelia and undissolved solids by conventional means, such as by filtration or centrifugation. The filtered broth, comprising paulomycin and antibiotic 273a$_1$, is then extracted, advantageously, with ethyl acetate at a pH of about 3.0. Other water-immiscible organic solvents, for example, chloroform, ethylene dichloride and methylene chloride can be used.

The organic extract of the filtered beer is separated and extracted with water at pH 5.5, (adjusted with NaOH). Paulomycin remains in the organic phase whereas the aqueous phase contains antibiotic 273a$_1$ and impurities. The aqueous solution, containing antibiotic 273a$_1$, is adjusted to pH 3.0 and extracted with ethyl acetate. Concentration of this solution yields a preparation rich in antibiotic 273a$_1$. Chromatography on a silica gel column can be used to obtain an essentially pure preparation of antibiotic 273a$_1$.

When antibiotic 273a$_1$ is subjected to high performance liquid chromatographic procedures (HPLC) there are obtained antibiotic 273a$_1\alpha$ and antibiotic 273a$_1\beta$.

Salts of the new antibiotics disclosed herein can be prepared by suspending the antibiotic in water and neutralizing with dilute solutions of a base. Freeze-drying of the neutralized solution provides a dried residue consisting of the desired antibiotic salt. Salts of the subject antibiotics can be used for the same biological purposes as the parent compounds.

Salts include the alkaline metal (including ammonia) and alkaline earth metal (including magnesium and aluminum) salts obtained by neutralizing the acid form of the antibiotic with the appropriate base, for example, ammonium hydroxide, sodium and potassium hydroxides, or alkoxides, calcium, or magnesium hydroxides, and the like. Salts also include amine salts obtained by neutralizing the acid form with a basic amine, for example, mono-, di-, and trimethylamines, mono-, di-, and triethylamines, mono-, di-, and tripropylamines (iso- and normal), ethyldimethylamine, benzyldiethylamine, cyclohexylamine, benzylamine, dibenzylamine, N,N'-dibenzylethylenediamine, bis-(orthomethoxyphenylisopropyl)amine, and the like lower-aliphatic, lower-cycloaliphatic and lower-araliphatic amines, the lower aliphatic and lower-cycloaliphatic radicals containing up to and including eight carbon atoms; heterocyclic amines such as piperidine, morpholine, pyrrolidine, piperazine, and the lower-alkyl derivatives wherein lower alkyl contains one to eight carbon atoms, inclusive thereof such as 1-methylpiperidine, 4-ethylmorpholine, 1-isopropylpyrrolidine, 1,4-dimethylpiperazine, 1-n-butylpiperidine, 2-methylpiperidine and 1-ethyl-2-methylpiperidine; amines containing water solubilizing or hydrophilic groups such as mono-, di-, and triethanolamines, ethyldiethanolamine, n-butyl-monoethanolamine, 2-amino-1-butanol, 2-amino-2-ethyl-1,3-propanediol, 2-amino-2-methyl-1-propanol, tris-(hydroxymethyl)-aminomethane, phenylmonoethanolamine, p-tertiaryamylphenyldiethanolamine, and gelactamine, N-methylgludamine, N-methylglucosamine, ephedrine, phenylephrine, epinephrine, and procaine; tetraethylammonium hydroxide; and guanidine.

Hereinafter are described non-limiting examples of the process and products of the subject invention. All percentages are by weight, and all solvent mixture proportions are by volume unless otherwise noted.

EXAMPLE 1

A. Fermentation

A biologically pure culture of *Streptomyces paulus* strain 273, NRRL12251, is used to inoculate a series of 500-ml. Erlenmeyer seed flasks, each containing 100 ml. of sterile seed medium consisting of the following ingredients:

| | |
|---|---|
| Glucose monohydrate | 25 g/l. |
| Pharmamedia* | 25 g/l. |
| Tap water q.s. | 1 liter |

*Pharmamedia is an industrial grade of cottonseed flour produced by Traders Oil Mill Company, Fort Worth, Texas.

The seed medium presterilization pH is 7.2. The seed inoculum is grown for 2 days at 28° C. on a Gump rotary shaker operating at 250 r.p.m. and having a 2½ inch stroke.

Seed inoculum (5%), prepared as described above, is used to inoculate a series of 500 ml. fermentation flasks containing 100 ml. of sterile fermentation medium consisting of the following ingredients:

| | |
|---|---|
| Malt extract | 30 g/l. |
| Cerelose | 10 g/l. |
| Soybean meal | 12 g/l. |
| Cornsteep liquor | 5 g/l. |
| UCON | 5 g/l. |
| Tap water q.s. | 1 liter |

Note: pH was adjusted to 7.2 before sterilization.

The inoculated fermentation flasks are incubated at a temperature of 25° C. for 3 to 5 days while being shaken on a Gump rotary shaker operating at 250 r.p.m. and having a 2½ inch stroke. Foaming in the fermentation flasks is controlled by the antifoam agent UCON (a synthetic defoamer supplied by Union Carbide, N.Y., N.Y.).

Antibiotic Assay

Fermentation beers are sedimented by centrifugation at ca. 3000Xg. The supernatant fluids (clear beers) are assayed for antibiotic activity vs. *S. lutea*, UC⊃130 using bioautographic or disc-plate methods. For bioautography, thin layer chromatography (tlc) is performed on Brinkman silica gel (Sil NHr plates) or on Brinkman cellulose (Cel 400) developed respectively in $CHCl_3$, $C_2H_5OH$ and $H_2O$ (25:30:5) or in 0.1M potassium phosphate, pH 7. Clear beer anti-*S. lutea* biounit titers are obtained by a standard disc-plate assay.

A biounit (BU) is defined as the concentration of the antibiotic which gives a 20 mm zone of inhibition under the above assay conditions. Thus, if for example a fermentation beer, or other solution containing the antibiotic, needs to be diluted 1/100 to give a 20 mm zone of inhibition, the potency of such beer or solution is 100 BU per ml.

B. Recovery

The whole beer (5000 L) is filtered using filter aid. The filtered beer (ca. 4500 L) is adjusted to pH 3.0 with 6N aqueous sulfuric acid. The acidified solution is extracted with 1000 L of Skellysolve B; the extract is found bioinactive and is discarded. The acidic clear filtrate is then extracted twice with 1500 L of ethyl acetate. The ethyl acetate extracts are combined and washed with 1000 L of water at pH 5.3 (AQUEOUS-1). The ethyl acetate extract is then concentrated to a volume of ca. 40 L and poured into 800 L of Skellysolve B under stirring. The precipitate is isolated by filtration and dried. (Preparation A, 95.4 g, 1400-VIII-62.1). The Skellysolve B filtrate is concentrated to an oil residue (Preparation B, 269 g, 1400-VIII-62.4). The aqueous solution, designated as AQUEOUS-1, is adjusted to pH 3.0 with aqueous hydrochloric acid and is extracted twice with 300 L of ethyl acetate. The ethyl acetate extracts are concentrated to a volume of 24 L and this solution mixed with 250 L of Skellysolve B. The precipitated material is isolated by filtration (Preparation C, 176.5 g, 1400-VIII-63.4). The filtrate is concentrated to dryness to give Prep. D, 1400-VIII-63.5, 39.6 g. Assay vs. *M. luteus* shows the following results.

| | |
|---|---|
| Prep. 1400-VIII-62.1 (Prep. A) | 160 bu/mg |
| -62.4 (Prep. B) | 1 bu/mg |
| -63.4 (Prep. C) | 52 bu/mg |
| -63.5 (Prep. D) | 2 bu/mg |

Preparation A contains (by tlc) paulomycins and other materials. Preparation C, designated Prep. 13913-ADA-61.3 contains paulomycins and antibiotic $273a_1$. (Ref. 13913-ADA-62). Preparations B and D were discarded.

Prep. 13913-ADA-61.3 is used for the isolation of antibiotic $273a_1$, as described below.

C. Silica Gel Chromatography

1. Preparation of Silica Gel

One kg. of silica gel (Merck-Darmstadt 7734) is triturated with 800 ml of a solution containing 38 g of KCl per L, adjusted to pH 2.0 with 1N aqueous hydrochloric acid. The KCl-HCl treated silica is activated by heating at 110° for 20 hours.

2. Preparation of the Starting Material

Prep. 13913-ADA-61.3, 115 g, isolated as described earlier, is dissolved in chloroform-ethanol-water (25:30:5 v/v); final solution, 500 ml; ca. 230 mg/ml. Part of this solution is used as the starting material for the chromatography described below.

3. Chromatography

Activated KCl-HCl treated silica gel, prepared as described above, is packed into a glass column using chloroform-ethanol-water (25:30:5) as the solvent system. The starting material, 43.5 ml (containing ca. 10 g of Prep. 13913-ADA-61.3) is added on the top of the column and is adsorbed on the silica bed. The column is eluted with the chloroform-ethanol-water system at the rate of 20 ml/minute. Fractions of 20 ml are collected and tested for bioactivity against *M. luteus*. Results are presented below.

| Fraction No. | Zone (mm) | Fraction No. | Zone (mm) |
|---|---|---|---|
| 20 | 0 | 420 | 33 |
| 40 | 0 | 440 | 32.5 |
| 60 | 0 | 460 | 32.5 |
| 80 | 31.5 | 480 | 31 |
| 100 | 30 | 500 | 21 |
| 120 | 28 | 520 | 30 |
| 140 | 22 | 540 | 28.5 |
| 160 | 18.5 | 560 | 26.5 |
| 180 | 26 | 580 | 25 |
| 200 | 21 | 600 | 23 |
| 220 | 20 | 620 | 19 |
| 240 | 20 | 640 | 18 |
| 260 | 19 | 660 | 16 |
| 280 | 19 | 680 | 15 |
| 300 | 19 | 700 | 0 |
| 320 | 19.5 | 720 | 0 |

-continued

| Fraction No. | Zone (mm) | Fraction No. | Zone (mm) |
| --- | --- | --- | --- |
| 340 | 22 | | |
| 360 | 26 | | |
| 380 | 29.5 | | |
| 400 | 32 | | |

Thin layer chromatographic analysis of the isolated fractions indicated the following:

| Fractions | Compound |
| --- | --- |
| 80 | Paulomycin |
| 340–600 | 273a$_1$ |

Fractions 340–600, containing antibiotic 273a$_1$, are combined (14130-ADA-36B). This solution is mixed with two volumes of cyclohexane. The lower phase, 1750 ml (14130-ADA-36C), the upper phase, 12.5 L (1400-ADA-36D) as well as Prep. 14130-ADA-36B are assayed (*M. luteus*).

| Prep. | FS | 1/4 | 1/8 | 1/16 | 1/32 | 1/64 |
| --- | --- | --- | --- | --- | --- | --- | --- |
| 14130-ADA-36B | 29.5 | 26.5 | 24 | 21 | 19 | 15.5 | 0 |
| -36C | 32.5 | 30.5 | 27.5 | 26 | 23 | 20.5 | 18 |
| -36D | 0 | 0 | 0 | 0 | 0 | 0 | 0 |

Prep. 14130-ADA-36C is concentrated to dryness to give preparation 14130-ADA-36.2 which contained (by tlc) antibiotic 273a$_1$.

Preparation 14130-ADA-36.2 is distributed between 200 ml of ethyl acetate and 200 ml of water at pH 3.0 (adjusted with 1N aqueous hydrochloric acid). The ethyl acetate phase is kept as EtOAc-1; the aqueous is extracted with 100 ml ethyl acetate (EtOAc-2). The ethyl acetate extracts -1 and -2 are combined, dried over sodium sulfate and concentrated to dryness in vacuo. The residue obtained is dissolved in 10 ml of methanol and this solution is mixed with 600 ml of ether and 400 ml of Skellysolve B. The precipitated material is isolated by filtration and dried to give preparation 14130-ADA-55.1, 460 mg. Assay (*M. luteus*), ca. 70–80 bu/mg. This is an essentially pure preparation of antibiotic 273a$_1$.

EXAMPLE 2

Preparation of Antibiotic 273a$_1\alpha$ and Antibiotic 273a$_1\beta$ From Antibiotic 273a$_1$ By HPLC For the HPLC, a gradient system is devised. The column is first eluted for 5 minutes isocractically with a mixture of 15% acetonitrile and 75% of 0.05M pH 5.5 phosphate buffer; then the percentage of acetonitrile in the mobile phase increases in a linear gradient so that the mobile phase contains 40% acetonitrile after 15 minutes. A typical HPLC chromatogram of antibiotics 273a$_1\alpha$ and 273a$_1\beta$ using these conditions is shown in FIG. 6. The retention times for the two antibiotics are 10.3 and 9.01 minutes, respectively. Essentially pure preparations of antibiotic 273a$_1\alpha$ and antibiotic 273a$_1\beta$ are recovered from the HPLC by extraction of the eluates with ethyl acetate at pH 3.0 (adjusted with aqueous HCl). The ethyl acetate extracts are concentrated to dryness and the residues obtained are further purified by precipitation from acetone-ether.

Biological testing of antibiotics 273a$_1$, 273a$_1\alpha$ and 273a$_1\beta$, show that these compounds have essentially the same antibacterial spectrum to that of the paulomycins disclosed in U.S. Pat. No. 4,335,108. Thus, these antibiotics are useful in the same manner as are the paulomycins.

We claim:

1. Essentially pure antibiotic 273a$_1$, which is characterized by the following characteristic spectra and other data:
   (a) an infrared absorption spectrum as shown in FIG. 1 of the drawings;
   (b) an ultraviolet absorption spectrum as shown in FIG. 2 of the drawings;
   (c) a proton magnetic resonance spectrum as shown in FIG. 3 of the drawings;
   (d) a C-13 nuclear magnetic resonance spectrum as shown in FIG. 4 of the drawings;
   (e) a mass spectrum as shown in FIG. 5 of the drawings;
   (f) an HPLC chromatogram as shown in FIG. 6 of the drawings;
   (g) a bioautogram in comparison with paulomycin as shown in FIG. 7 of the drawings;
   (h) a melting point of ca. 120° C. with decomposition;
   (i) an optical rotation $[\alpha]_D^{25}$, $\sim 33°$ (C, 0.890, methanol);
   (j) elemental analysis: Calcd for a mixture of 60% 273a$_1\alpha$ and 40% 273a$_1\beta$: C, 47.24; H, 5.70; N, 5.06; S, 8.68; found: C, 46.42; H, 5.68; N, 4.90; S, 8.73; and, salts thereof with inorganic and organic bases.

2. Essentially pure antibiotic 273a$_1\alpha$, which is characterized by the following characteristic spectra and other data:
   (a) an infrared absorption spectrum as shown in FIG. 8 of the drawings;
   (b) an ultraviolet absorption spectrum as shown in FIG. 9 of the drawings;
   (c) a proton magnetic resonance spectrum as shown in FIG. 10 of the drawings;
   (d) a C-13 nuclear magnetic resonance spectrum as shown in FIG. 11 of the drawings;
   (e) a mass spectrum as shown in FIG. 12 of the drawings;
   (f) an HPLC chromatogram as shown in FIG. 13 of the drawings;
   (g) a melting point of ca. 120° C. with decomposition;
   (h) an optical rotation $[\alpha]_D^{25} - 31°$ (C, 0.905 methanol);
   (i) elemental analysis: Calcd for $C_{44}H_{64}N_4O_{23}S_3$: C, 47.48; H, 5.75; N, 5.03; S, 8.63; found: C, 46.82; H, 5.78; N, 4.93; S, 8.72;
   (j) molecular weight of 1112; and, salts thereof with inorganic and organic bases.

3. Essentially pure antibiotic 273a$_1\beta$, which is characterized by the following characteristic spectra and other data:
   (a) an infrared absorption spectrum as shown in FIG. 14 of the drawings;
   (b) an ultraviolet absorption spectrum as shown in FIG. 15 of the drawings;
   (c) a proton magnetic resonance spectrum as shown in FIG. 16 of the drawings;
   (d) a C-13 nuclear magnetic resonance spectrum as shown in FIG. 17 of the drawings;
   (e) a mass spectrum as shown in FIG. 18 of the drawings;
   (f) an HPLC chromatogram as shown in FIG. 19 of the drawings;
   (g) a melting point of ca. 120° C. with decomposition;

(h) an optical rotation $[\alpha]_D^{25}$, $-35°$ (C, 0.908, methanol);

(i) elemental analysis: Calcd for $C_{43}H_{62}N_4O_{23}S_3$: C, 46.99; H, 5.64; N, 5.10; S, 8.74; found: C, 46.22; H, 5.69; N, 5.00; S, 8.83;

(j) molecular weight of 1098; and, salts thereof with inorganic and organic bases.

* * * * *